US012582829B2

(12) United States Patent
Fourkas et al.

(10) Patent No.: US 12,582,829 B2
(45) Date of Patent: Mar. 24, 2026

(54) PLASMA TREATMENT DEVICES AND METHODS OF USE THEREOF

(71) Applicant: TheraDep Technologies, Inc., Palo Alto, CA (US)

(72) Inventors: Michael Fourkas, Sunnyvale, CA (US); Denis O'Sullivan, Dungarvan (IE); Liam O'Neill, Midleton (IE); Joseph M. Tartaglia, Morgan Hill, CA (US)

(73) Assignee: TheraDep Technologies, Inc., Palo Alto, CA (US)

( * ) Notice: Subject to any disclaimer, the term of this patent is extended or adjusted under 35 U.S.C. 154(b) by 1196 days.

(21) Appl. No.: 17/600,516

(22) PCT Filed: Mar. 30, 2020

(86) PCT No.: PCT/US2020/025685
§ 371 (c)(1),
(2) Date: Sep. 30, 2021

(87) PCT Pub. No.: WO2020/205718
PCT Pub. Date: Oct. 8, 2020

(65) Prior Publication Data
US 2022/0176140 A1    Jun. 9, 2022

Related U.S. Application Data

(60) Provisional application No. 62/828,797, filed on Apr. 3, 2019.

(51) Int. Cl.
*A61N 1/44* (2006.01)
*A61M 11/02* (2006.01)
*H05H 1/48* (2006.01)

(52) U.S. Cl.
CPC .............. *A61N 1/44* (2013.01); *A61M 11/02* (2013.01); *H05H 1/48* (2013.01); *H05H 2245/32* (2021.05); *H05H 2245/34* (2021.05)

(58) Field of Classification Search
CPC ....... A61N 1/44; A61N 1/0412; A61M 11/02; H05H 1/48; H05H 2245/32; G01N 21/714;
(Continued)

(56) References Cited

U.S. PATENT DOCUMENTS

| | | | |
|---|---|---|---|
| 5,554,172 A | 9/1996 | Horner et al. | |
| 2007/0006814 A1 | 1/2007 | Mead et al. | |

(Continued)

FOREIGN PATENT DOCUMENTS

| | | |
|---|---|---|
| CN | 101888860 A | 11/2010 |
| CN | 203763232 U | 8/2014 |

(Continued)

OTHER PUBLICATIONS

O'Neill, L. et al., "Evaluation of the J-Plasma Electrosurgical Device Combined with Nebulized Collagen for Burn Healing in Rodents", *Plasma Medicine*, pp. 365-377, (Jan. 1, 2018).

(Continued)

*Primary Examiner* — Xiuyu Tai

(74) *Attorney, Agent, or Firm* — Bookoff McAndrews, PLLC

(57) ABSTRACT

Medical devices for generating an aerosol and plasma, e.g., for therapeutic treatment are described. The medical device may include a nebulizer, the nebulizer including an outer compartment, an inner compartment, and a needle radially inward of the inner and outer compartments. The medical device may include at least one electrode and a chamber, wherein a distal-facing surface of the chamber defines at least one plasma outlet and a nozzle in communication with the nebulizer, an end of the electrode being proximate the plasma outlet.

29 Claims, 9 Drawing Sheets

(58) Field of Classification Search
CPC .... G01N 27/62; G01N 1/38; G01N 2001/002;
G01N 2001/387; G01N 21/73; G01N
27/626; B05B 15/52; B05B 7/22; B05B
7/2494; B05B 7/066; A61K 9/16; A61K
41/00; A61K 31/545; A61K 31/7036;
A61K 31/65; A61K 31/43; A61K 9/0014;
A61K 47/14; A61K 9/12; A61L 2/14;
A61L 2/0011; A61L 2202/11; A61L
29/08; A61L 31/08; A61L 31/16; A61L
29/16; A61L 27/54; A61L 2420/02; A61L
27/28; B05D 3/145; B05D 3/0254; B05D
1/62; B05D 7/54; B05D 2401/32; B01L
3/5085; B01L 2200/12; A61B
2018/00589; A61B 18/042; A61P 31/04
See application file for complete search history.

(56) References Cited

U.S. PATENT DOCUMENTS

| | | |
|---|---|---|
| 2011/0101862 A1 | 5/2011 | Koo et al. |
| 2012/0089084 A1 | 4/2012 | O'Keeffe et al. |

| | | |
|---|---|---|
| 2013/0218069 A1 | 8/2013 | Neugebauer et al. |
| 2015/0038790 A1 | 2/2015 | Ronta et al. |
| 2015/0366042 A1 | 12/2015 | Zaidi |
| 2017/0312376 A1 | 11/2017 | Bae |
| 2018/0296813 A1* | 10/2018 | Hoekman ............. A61M 15/08 |

FOREIGN PATENT DOCUMENTS

| | | | |
|---|---|---|---|
| EP | | 1588730 A1 | 10/2005 |
| EP | | 2765592 A2 | 8/2014 |
| EP | | 3415172 A1 | 12/2018 |
| JP | | H05245202 A | 9/1993 |
| JP | | H10 188877 A | 7/1998 |
| JP | | 2008519411 A | 6/2008 |
| JP | | 5245202 B2 | 7/2013 |
| JP | | 2014212839 A | 11/2014 |
| WO | WO 2009/100383 A2 | | 8/2009 |
| WO | | 2011069135 A1 | 6/2011 |

OTHER PUBLICATIONS

International Search Report in PCT/US2020/025685 mailed Jun. 22, 2020 (4 pages).

* cited by examiner

PLASMA TREATMENT DEVICES AND METHODS OF USE THEREOF

CROSS-REFERENCE TO RELATED APPLICATIONS

This application is the U.S. national phase entry under 35 U.S.C. § 371 of International Application No. PCT/US2020/025685, filed on Mar. 30, 2020, which claims priority to U.S. Provisional Application No. 62/828,797, filed Apr. 3, 2019, which is incorporated herein by reference in its entirety.

TECHNICAL FIELD

The present disclosure generally relates to a plasma treatment device, and methods of use thereof.

BACKGROUND

Plasma devices are used in medicine for surgery and sterilization techniques. Outside of medicine, plasma devices are used to produce thin film coatings, such as polymer coatings, in industrial applications. Methods of deposited polymers with plasma devices are often reliant upon the presence of a precursor which can react in the plasma to form the polymer coating during the deposition process. Such conditions may induce polymerization, but also can damage various species present in the plasma.

SUMMARY

The present disclosure includes medical devices for generating an aerosol and plasma, e.g., for therapeutic treatment. For example, the medical device may comprise a housing that includes a nebulizer, the nebulizer comprising an outer compartment in communication with a gas inlet, an inner compartment in communication with a fluid channel and a fluid inlet, and a needle; wherein the needle is radially inward of the inner compartment, the inner compartment is radially inward of the outer compartment, and a distal end of the outer compartment is in communication with a distal end of the inner compartment; at least one electrode; and a chamber defined by a distal end portion of the housing; wherein a distal-facing surface of the chamber defines at least one plasma outlet and a nozzle in communication with the nebulizer; and wherein an end of the electrode is proximate the plasma outlet.

In examples herein, the proximal portion of the chamber may be configured to receive an electrode tip of a plasma device and to electrically connect the electrode tip of the plasma device to the electrode of the plasma outlet and/or distal portion of the housing may include an actuator configured to control the flow of a gas to the gas inlet. A longitudinal position of the needle of the nebulizer may be adjustable.

According to some embodiments of the present disclosure, the medical device may further comprise a plasma device, wherein the actuator of the housing may be arranged relative to an actuator of the plasma device so as to allow a user to control the flow of gas and to power the plasma device simultaneously. In other examples, the medical device may further comprise a fluid reservoir coupled to the fluid inlet. The fluid reservoir may include mating elements complementary to mating elements of the fluid inlet, such that the fluid reservoir is selectively detachable from the fluid inlet. In at least one example, the fluid reservoir contains a liquid that comprises at least one therapeutic agent.

According to some aspects of the present disclosure, the at least one therapeutic agent comprises a biomolecule, a pharmaceutical agent, or a combination thereof. In some examples, the at least one therapeutic agent is dissolved in a solvent.

In some examples herein, the housing defines a first channel in communication with the outer compartment of the nebulizer and a second channel that contains the electrode, a distal end of the second channel defining the plasma outlet. In at least one example, the at least one electrode extends through a wall of the chamber.

The present disclosure also includes a medical device comprising a housing that includes a nebulizer, the nebulizer comprising an outer compartment, an inner compartment, and a needle; wherein the needle is radially inward of the inner compartment, the inner compartment is radially inward of the outer compartment, and a distal end of the outer compartment is in communication with a distal end of the inner compartment; a fluid reservoir coupled to a fluid inlet, the fluid reservoir containing a liquid that comprises at least one therapeutic agent; at least one electrode; and a chamber defined by a distal end portion of the housing; wherein a distal-facing surface of the chamber defines at least one plasma outlet and a nozzle in communication with the nebulizer; and wherein an end of the electrode is proximate the plasma outlet.

In some embodiments of the present disclosure, the fluid reservoir may include mating elements complementary to mating elements of the fluid inlet, such that the fluid reservoir is selectively detachable from the fluid inlet. In at least one example, the fluid reservoir is permanently attached to the fluid inlet. In some examples, the outer compartment of the nebulizer is in communication with a gas inlet, and the inner compartment of the nebulizer is in communication with the fluid inlet. In at least one example, the end of the electrode is recessed from the distal-facing surface of the chamber. According to some aspects of the present disclosure, the housing defines a first channel in communication with the outer compartment of the nebulizer and a second channel that contains the electrode, a distal end of the second channel defining the plasma outlet. In at least one example, the at last one therapeutic agent comprises a biomolecule, a pharmaceutical agent, or a combination thereof.

The present disclosure also includes a medical device comprising a housing that includes a nebulizer, the nebulizer comprising an outer compartment in communication with a gas inlet, an inner compartment in communication with a fluid inlet, and a needle; wherein the needle is radially inward of each of the inner compartment and the outer compartment, and a distal end of the outer compartment is in communication with a distal end of the inner compartment; at least one electrode; a fluid reservoir coupled to the fluid inlet; and a chamber defined by a distal end portion of the housing; wherein a distal-facing surface of the chamber defines at least one plasma outlet and a nozzle in communication with the nebulizer; and wherein an end of the electrode is proximate the plasma outlet.

The present disclosure also includes a methods of treating tissue of a subject. For example, the method may comprise exposing the tissue to plasma and/or an aerosol comprising at least one therapeutic agent using any of the medical devices as described herein. The tissue may be internal tissue or external tissue. In some examples, the tissue may be part of a wound, burn, cut, ulcer, abrasion, or tumor. In at least one example, the subject is a human subject. In some examples, the method comprises generating plasma at a frequency ranging from about 150 kHz to about 500 kHz.

According to some aspects of the present disclosure, the at least one therapeutic agent comprises a biomolecule, a pharmaceutical, or a combination thereof. In some examples, the at least one therapeutic agent comprises collagen.

The method may further include supplying a fluid to the nebulizer and supplying power to the at least one electrode simultaneously, such that an aerosol exits the nozzle at the same time a plasma exits the plasma outlet. Supplying the fluid and supplying the power may include pressing a single actuator of the medical device. In at least one example, pressing the single actuator and supplying the power may include pressing a single actuator of the medical device.

BRIEF DESCRIPTION OF THE DRAWINGS

The accompanying drawings, which are incorporated in and constitute a part of this specification, illustrate certain features of the present disclosure, and together with the description, serve to explain the principles of the present disclosure. Those of ordinary skill in the art will readily recognize that the features of a particular aspect or embodiment may be used in conjunction with the features of any or all of the other aspects or embodiments described in this disclosure.

DETAILED DESCRIPTION

Figure 1:
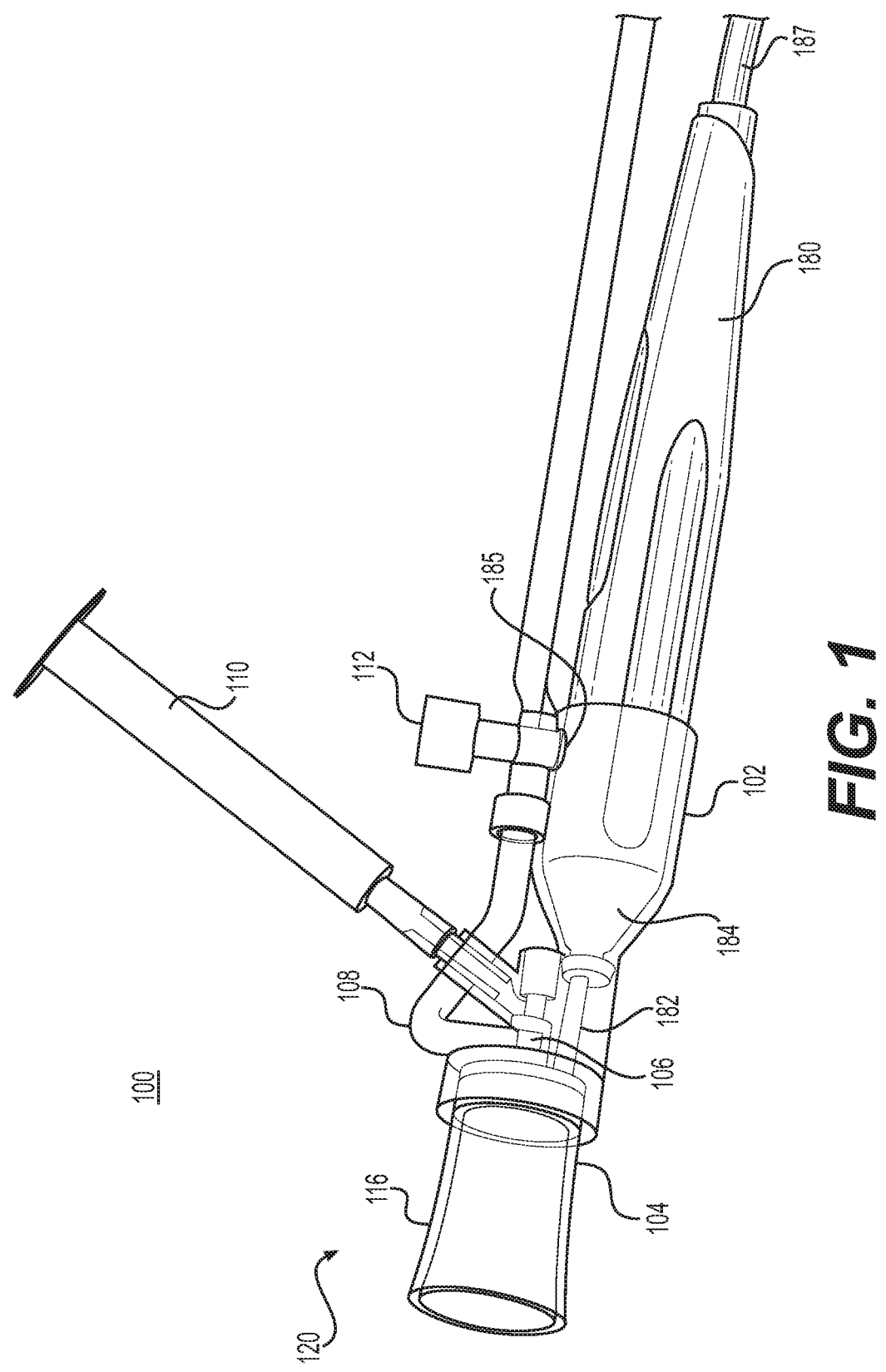
FIG. 1 illustrates an exemplary delivery device, in accordance with some aspects of the present disclosure.

The present disclosure generally includes systems, devices, and methods for delivering active therapeutic agents (e.g., biomolecules, pharmaceutically active agents, and/or combinations thereof) along with a plasma to a surface (e.g., a tissue surface or non-tissue substrate).

The singular forms "a," "an," and "the" include plural reference unless the context dictates otherwise. The terms "approximately" and "about" refer to being nearly the same as a referenced number or value. As used herein, the terms "approximately" and "about" generally should be understood to encompass ±5% of a specified amount or value. All ranges are understood to include endpoints, e.g., a distance between 1.0 cm and 5.0 cm includes distances of 1.0 cm, 5.0 cm, and all values between.

The systems and devices herein may be used to apply therapeutic agents to external and/or internal tissue of a subject, such as a human or non-human animal. For example, the therapeutic agent(s) and/or plasma may assist in healing. The systems and devices herein may be configured to deliver one or more therapeutic agents in a plasma and/or adjacent to a plasma, and may be configured to deliver the therapeutic agent(s) before, during, and/or after treating tissue with the plasma. The therapeutic agent(s) may be delivered, for example, via an aerosol proximate and/or mixed with a plasma, as described further below. In some examples, the therapeutic agent(s) comprise one or more pharmaceutical agents and/or biomolecules that do not contain vinyl groups or other chemical functional groups expected to polymerize under non-thermal equilibrium plasma conditions. The systems and devices herein may be used to treat various medical conditions, including, but not limited to, internal and/or external burns, wounds, cuts, incisions, ulcers, abrasions, and tumors.

The plasma may be a non-thermal equilibrium or cold plasma, e.g., to minimize damage to the therapeutic agent(s), tissue damage, and/or subject discomfort. For example, the plasma may be powered at a frequency ranging from about 150 kHz to about 500 kHz, such as from about 200 kHz to about 450 kHz, or from about 150 kHz to about 300 kHz. In some examples herein the maximum frequency may be less than 900 kHz, such as less than 700 kHz, for example less than 600 kHz. In at least one aspect, the plasma is a pulsed plasma. The plasma may be pulsed at various duty cycles such that the power delivered is less than 100 W, e.g., less than 20 W, or less than 10 W. The pulsing may be such that the applied power is off for at least 50% of the time, e.g., with the pulses switched on and off many times per second. For example, the plasma may be pulsed on and off to deliver an on-time ranging from about 1 ns to about 500 ms. For example, the plasma may be pulsed with an on-time ranging from 1 ms to 500 ms, such as from 10 ms to 300 ms, from 50 ms to 100 ms, e.g., an on-time of about 1 ms, about 10 ms, about 50 ms, about 75 ms, about 100 ms, about 200 ms, about 250 ms, about 300 ms, about 400 ms, or about 500 ms. For example, for the treatment of tissue, the plasma may be a nano-second or pico-second pulsed plasma. In these examples, the plasma may be only turned on for fractions of a millisecond for each pulse, e.g. less than 500 ns or less than 100 ns.

While exemplary devices are described herein and illustrated with given configurations and components, it will be apparent to those of ordinary skill in the art that variations of the devices are also encompassed herein. For example, components of the devices illustrated in the figures may be arranged in different configurations or may be omitted completely. Further, additional components may be added to the devices, in view of the discussion herein and in accordance with the principles disclosed.

FIGS. 1-3B illustrate features of an exemplary device 100 that may be used to deliver one or more therapeutic agents in conjunction with a plasma. For example, FIG. 1 shows a device 100 that includes an adapter 120 coupled to a plasma device 180 for generating a non-thermal plasma. The plasma device 180 includes a body with a power button 185, and a distal end portion 184 that includes a distal tip 182. The distal tip 182 may include electrodes coupled to a power source and a source of gas controlled by the power button 185. Thus, engaging the power button 185 of the plasma device 180 initiates a concurrent delivery of gas and alternating electric current to the distal tip 182 to generate plasma. The adapter 120 may be configured to couple to the distal end portion 184 of the plasma device 180, e.g., in a detachable manner. The adapter may allow for simultaneous and/or sequential deposition of aerosol containing one or more therapeutic agents with plasma generated by the plasma device 180.

As shown in FIG. 1, the adapter 120 includes a proximal opening 102 for receiving the distal end portion 184 of the plasma device 180. The adapter 120 may be secured to the plasma device 180 via any suitable connection or mechanism, for example, friction fit (e.g., an inner surface of the proximal opening 102 comprising an elastomeric material), clips, screws, threads, etc. The adapter 120 further includes a distal end portion 104 that defines an outlet chamber 116, a nebulizer 106, a gas inlet 108, and a fluid reservoir 110. The gas inlet 108 may be coupled to a source of gas, such as a medical gas system or portable cylinder of compressed gas. Exemplary gases that may be used with the devices and systems herein include, but are not limited to, air (including medical air), nitrogen, helium, argon, and mixtures thereof. The gas inlet 108 and the fluid reservoir 110 are in communication with the nebulizer 106. The fluid reservoir 110 may be permanently attached to, or integral with, the adapter 120, or the fluid reservoir 110 may be coupled to the adapter 120 via suitable connector, such as a luer fitting. In some examples herein, the fluid reservoir 110 may be in the form of a syringe. FIGS. 5A-5E illustrate additional examples of fluid reservoirs that may be used with device 100 and/or any other devices herein.

The gas may be regulated at a fixed or varied pressure and/or flow rate. For example, the gas may be regulated at a pressure of about 30 psi to about 40 psi, e.g., about 35 psi. In some embodiments of the present disclosure, the flow of gas used to generate the plasma may range from about 1 liters/min (L/min) to about 10 L/min, such as from about 1 L/min to about 5 L/min, from about 5 L/min to about 7 L/min, or from about 4 L/min to about 6 L/min.

Figure 2:
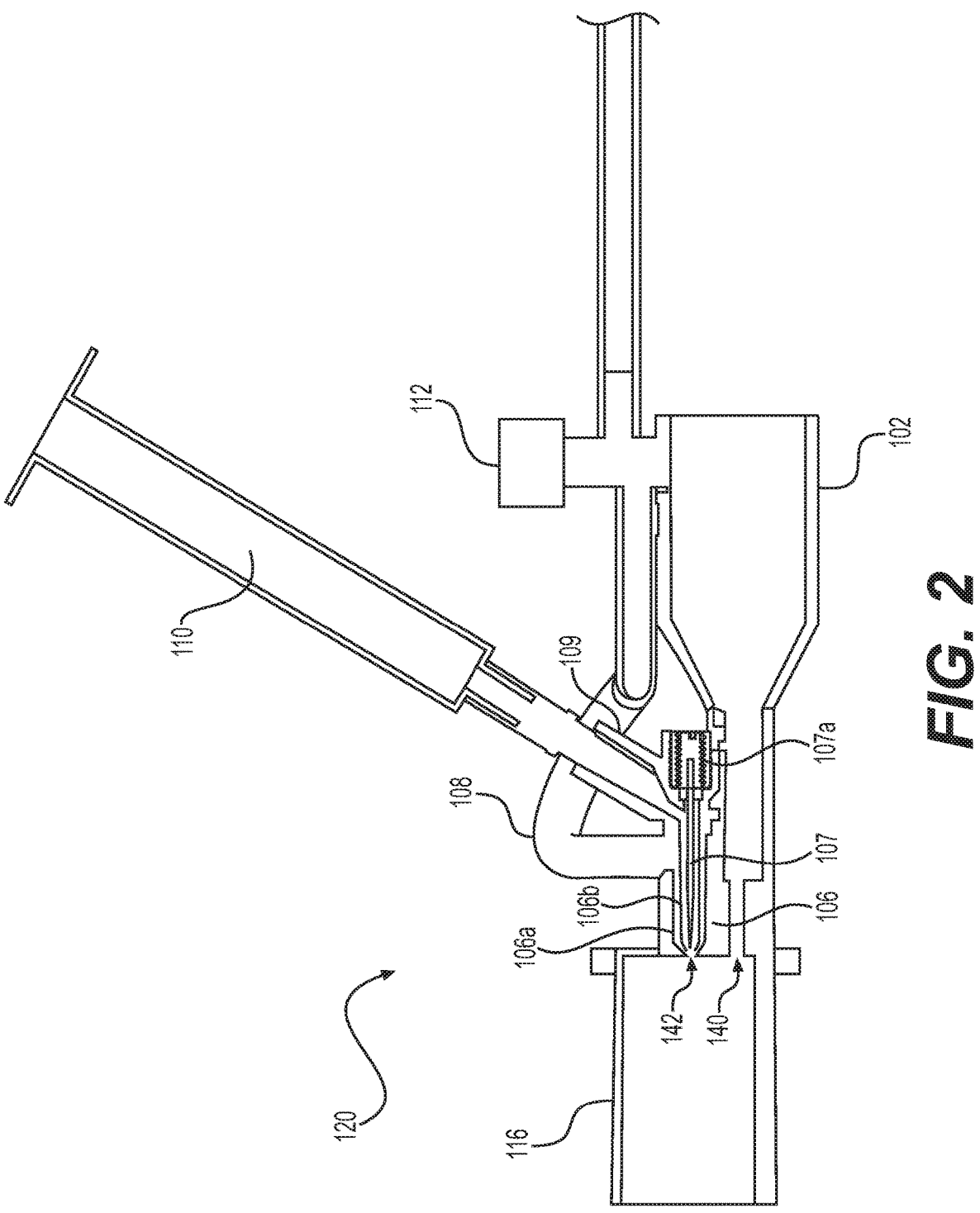
FIG. 2 shows a cross-sectional view of the device of FIG. 1.

The adapter 120 further includes an actuator 112 configured to control the flow of gas to the nebulizer 106, e.g., via a valve (which may be mechanical or electrical). Thus, for example, a user may control the flow of gas to the adapter 120 via the actuator 112, which in turn may control generation of an aerosol via the nebulizer 106. That is, initiating the flow of gas to the gas inlet 108 results in a pressure change in the nebulizer 106. Fluid contained within the fluid reservoir 110 may be in communication with the nebulizer 106, such that the change in pressure pulls fluid from the fluid reservoir 110 into the nebulizer 106. Thus, for example, the fluid may be drawn into the nebulizer 106 without external forces or systems to push to the fluid into the nebulizer 106, such as an external pump, a liquid delivery system, or external pressurization. That is, the change in pressure may be sufficient to draw fluid from the fluid reservoir 110. The gas and fluid then exit the nebulizer 106 via a nozzle 142 of the distal end portion 104 of the adapter 120. Further details of the nebulizer 106 are shown in FIG. 2.

Further referring to FIG. 1, the actuator 112 may be arranged such that, when the adapter 120 is coupled to the plasma device 180, the actuator 112 is superimposed over the power button 185 to allow a user to generate aerosol and plasma simultaneously. Thus, for example, once the plasma device 180 is engaged with the adapter 120 (e.g., the distal end portion 184 of the plasma device 180 being inserted into the proximal opening 102 of the adapter 120), depressing the actuator 112 may open a valve to a gas supply and also engage the power button 185 of the plasma device 180. Plasma generated by the plasma device 180 may enter the chamber 116 via one or more plasma outlets 140.

According to some examples herein, the actuator 112 may be configured to allow the user to control the aerosol and plasma separately and independently. For example, the actuator 112 may include a first portion that engages the valve to the gas supply and a second portion that engages the power button 185, wherein the first and second portions may be pressed separately, in sequence, or simultaneously.

The fluid reservoir 110 may be open-ended or closed-ended, such as topped with a plunger or cap to prevent fluid from spilling out of the fluid reservoir 110. In some examples, the fluid reservoir 110 may include a plunger or cap that is vented, e.g., to equalize pressure as liquid leaves. The fluid reservoir 110 may be coupled to the nebulizer 106 at an appropriate angle to allow fluid contained within the fluid reservoir 110 to flow into a channel in communication with the nebulizer 106 by gravity. According to some aspects of the present disclosure, the fluid reservoir 110 may be positioned at an angle less than 90 degrees relative to the longitudinal axis of the nebulizer 106. For example, the fluid reservoir 110 may be at an angle ranging from about 10 degrees to about 85 degrees or about 30 degrees to about 60 degrees, such as an angle of about 80 degrees, about 70 degrees, about 60 degrees, about 50 degrees, or about 40 degrees.

The fluid contained in the fluid reservoir 110 may comprise any appropriate liquid compatible with the therapeutic agent and suitable for generating an aerosol. The liquid may comprise, consist of, or consist essentially of one or more therapeutic agents. The therapeutic agent(s) may be dissolved or otherwise mixed with a solvent such as water or other aqueous solution, or an alcohol or other organic solvent, among other examples. Exemplary solvents include, but are not limited to, acetic acid and acetic acid solutions, ethanol and ethanol solutions, water including acidified water (e.g., with a pH greater than 3 but less than 7), saline solutions, solutions containing free amino acids, sulphate solutions, polyelectrolytes such as polyphosphate or sulphated polysaccharides, complexing agents, and mixtures thereof. In some embodiments, the solvent may comprise an organic solvent, such as, e.g., an alcohol, such as methanol, ethanol, propanol, butanol, polyvinyl alcohol, benzoyl alcohol, a fatty alcohol, a lanolin alcohol, glycerol, ethylene glycol, polyethylene glycol, and mixtures thereof; dimethyl sulfoxide (DMSO); isopropyl myristate; oleic acid; acetone; chloroform; ethyl acetate; azone (laurocapram); urea; essential oils; fatty acids; oxazolidinones; terpene; perpenoids; and mixtures thereof. Further exemplary organic solvents include organic compounds such as pyrrolidone, e.g., polyvinylpyrrolidone (PVP), cyclodextrins, dissolved in a suitable liquid, such as water or organic liquid.

Exemplary therapeutic agents that may be delivered with the devices herein include, but are not limited to, pharmaceutical agents, biomolecules, and mixtures thereof. In some embodiments, the liquid may comprise one or more pharmaceutically active materials, biomolecules, antibiotics, penetration enhancing agents, carriers, antiseptics, proteins, biopolymers, synthetic biodegradable polymers, or combinations thereof. Exemplary therapeutic agents include, but are not limited to, collagen, fibrin, elastin, fibronectin, hyaluronan, chitosan, alginates, cellulose, phosphorylcholine, polypeptides, polyglycans, hormones, lipids, interferons, cartilage, recombinant blood cells, synthetic derived blood cells, platelet-rich plasma, cells (autologous or donor cells), melanocytes, stem cells, antimicrobials, antibiotics, bacteriostatic agents, antibodies (including monoclonal antibodies), stem cells, amniotic membrane materials, bovine serum albumin, proteins, clotting factors, growth factors, cytokines, chemotherapy agents, anti-inflammatory drugs, immune-suppressants, analgesics, blood pressure medications, antithrombotics, anticoagulants, antiplatelet agents, thrombolytics, antiproliferatives, antimitotic, agents that inhibit restenosis, smooth muscle cell inhibitors, fibrinolytic, immunosuppressive, anti-antigenic agents, vaccines, and combinations thereof. For example, the liquid may comprise collagen, blood plasma, chitosan, or combinations thereof.

Referring to FIGS. 1 and 2, nebulizer 106 may be any appropriate atomizer or nebulizer, including, e.g., ultrasonic, piezo, pneumatic, mechanical, electrical, vibrating mesh, or jet nebulizers. The nebulizer 106 may comprise an outer compartment 106*a*, inner compartment 106*b*, needle 107, and threaded connection 107*a*. The outer compartment 106*a* and the inner compartment 106*b* may be concentric with each other and arranged such that the distal outlet of the outer compartment 106*a* is in communication with the distal outlet of the inner compartment 106*b*. The needle 107 may be radially inward of both the outer compartment 106*a* and the inner compartment 106*b*, e.g., contained within the inner compartment 106*b*.

According to some aspects of the present disclosure, the fluid reservoir 110 may be disposed relatively close to the nebulizer. For example, the fluid reservoir 110 may be disposed less than about 50 mm from the nebulizer 106, e.g., from about 1 mm to about 50 mm. For example, the fluid reservoir 110 may be disposed less than about 45 mm, less than about 40 mm, less than about 35 mm, less than about 30 mm, or less than about 25 mm from the nebulizer 106. Without intending to be bound to theory, it is believed that the placement of the fluid reservoir 110 relatively close to the nebulizer 106 may provide for efficient transport of fluid. For example, fluid may be supplied to the nebulizer without a syringe pump or tubing or other liquid line.

The outer compartment 106*a* may be in communication with a source of gas, and the inner compartment 106*b* may be in communication with a source of fluid. For example, as shown in FIG. 2, gas inlet 108 connects a gas source to the outer compartment 106*a* of the adapter 120, such that gas is fed through the gas inlet 108, and into the outer compartment 106*a* of the nebulizer 106. Similarly, fluid inlet 109 connects a fluid source (e.g., fluid reservoir 110) to the inner compartment 106*b*. As discussed above, fluid contained within the fluid reservoir 110 may enter a fluid channel in communication with the inner compartment 106*b* of the nebulizer 106. Thus, for example, when the gas flow is turned on, a change in pressure within the adapter 120 may pull fluid from the fluid reservoir 110 into the inner compartment 106*b*. The gas and fluid then exits the respective distal outlets of the outer compartment 106*a* and the inner compartment 106*b* as an aerosol via a nozzle 142 of the distal end portion 104 of the adapter 120. The aerosol exiting the nozzle 142 is introduced into the outlet chamber 116, such that the aerosol can mix with plasma entering the chamber 116 via the plasma outlet(s) 140 adjacent to the nozzle 142 prior to contact with the surface to be treated with the plasma and therapeutic agent(s). The outlet chamber 116 may have dimensions defining a volume sufficient for mixing the aerosol with the plasma prior to deposition onto a surface, such as tissue of a subject to be treated. The outlet chamber 116 may have various shapes, for example, a conical shape, wherein the distal end of the outlet chamber 116 may flare out, such that the cross-sectional dimension of the distal end of the chamber 116 is greater than the cross-sectional dimension of the proximal end of the chamber 116. A flared conical shape may allow the plasma and aerosol to spray out and cover a relatively larger surface area to be treated. In some examples, the chamber 116 may narrow at the distal end, e.g., providing for a more targeted or focused stream of aerosol and plasma on the surface to be treated. According to some aspects of the present disclosure, the length of the chamber ranges from about 10 mm to about 100 mm, such as from about 30 mm to about 50 mm, or from about 35 mm to about 45 mm. Further, for example, the chamber may have a cross-sectional shape with an inner diameter ranging from about 6 mm to about 50 mm, such as from about 10 mm to about 30 mm, or from about 15 mm to about 25 mm.

In an example of the present disclosure, the outer compartment 106*a* and the inner compartment 106*b* may taper towards the needle 107 at or proximate the nozzle 142. In some examples, the tip of the needle 107 may be flush with the proximal wall of the outlet chamber 116, or the tip may protrude into the outlet chamber 116. In either case, the tip of the needle 107 may be disposed relative to the nozzle 142 so as to allow aerosol to enter the chamber 116.

Without intending to be bound to theory, it is believed that the reduction in radial cross section of the outer and inner compartments 106*a*, 106*b* may allow for acceleration of gas and liquid flow, and in turn, reduced pressure. This change in pressure provides a venturi effect on the inner compartment 106*b*, wherein the pressure is lower at the distal outlet of the inner compartment 106*b* relative to the pressure in the fluid reservoir 110. When the outer compartment 106*a* becomes pressurized, fluid contained in the reservoir 110 is drawn into the inner compartment 106*b* of the nebulizer 106. The liquid exiting the inner compartment 106*b* over the tip of the needle 107 may be atomized by gas exiting the outer compartment 106*a* through the nozzle 142 to produce an aerosol in the outlet chamber 116.

In some examples of the present disclosure, the distal end of the outer compartment 106*a* is in communication with the distal end of the inner compartment 106*b* via an opening that has an annular shape. For example, the opening may have a uniform annular shape, which may result in a uniform flow of gas exiting from the outer compartment 106*a* and contacting liquid from the inner compartment 106*b*, then exiting through the nozzle 142 into the outlet chamber 116. Adjusting the shape and/or size of the opening, e.g., by adjusting the position of the needle 107, may alter the flow of gas and as a result, the shape and/or volume of the resulting spray. For example, a flat orifice may produce a fan-shaped spray. In an embodiment of the present disclosure, the spray of the atomized fluid has a uniform conical shape. Additionally, reducing the annular distance between the inner diameter of the outer compartment 106*a* and the outer diameter of the inner compartment 106*b* may increase the velocity of the gas exiting from the distal end of the outer compartment 106*a*. The increase in gas flow velocity is expected to further reduce the pressure at the distal end of the inner compartment 106*b*.

According to some aspects of the present disclosure, there is a uniform annular opening between the inner compartment 106*b* and the tip of the needle 107. The size of the annular opening may restrict the amount of fluid exiting from the distal end of the inner compartment 106*b*. Without intending to be bound to theory, the orientation of the distal end of the needle 107, and the respective distal ends of the inner compartment 106*b* and outer compartment 106*a*, may characterize the performance of the nozzle 142 in generating aerosol. The outer compartment 106*a* may have a nozzle throat, wherein the nozzle throat corresponds to the smallest diameter portion of the distal end of the outer compartment 106*a*. The dimension of the throat relative to the rest of the nozzle 142 and the inlet gas pressure may determine the pressure in the nozzle 142, and therefore the strength of the venturi effect. The distal end of the inner compartment 106*b* may be at or proximate a portion of the outer compartment's 106*a* nozzle throat or outside the outer compartment 106*a* nozzle throat so the pressure at the nozzle throat is lower than the pressure in the fluid reservoir 110. Otherwise, the pressure in the nozzle may be above atmospheric pressure, which may prevent flow of the fluid from the fluid reservoir 110 into the inner compartment 106*b* and instead gas may flow into the fluid reservoir 110. The distal end of the inner compartment 106*b* may also be sufficiently close to the distal end of the outer compartment 106*a* such that the gas flow may atomize the liquid. If the distal end of the inner compartment 106*b* is too far from the distal end of the outer compartment 106*a*, the liquid may form relatively large droplets.

The threaded connection 107*a* of the nebulizer 106 may be attached to or integral with a proximal end of the needle 107, wherein the threaded connection 107*a* may be mated with internal threads at a proximal portion of the inner compartment 106*b*. The needle 107 may be retracted or advanced by rotating the threaded connection 107*a*, which in turn may increase or decrease the flow of aerosol from the nozzle 142. The threaded connection 107*a* may be fixed or adjustable. In examples of the present disclosure, the needle 107 may be advanced and seated against an inner surface of the distal end of the inner compartment 106*b*. Further advancing the needle 107 may result in a slight deformation of the distal end of the inner compartment 106*b*, such that the distal end is positioned within the distal end of the outer compartment 106*a*. Retracting the needle 107 sets the annular space between the needle 107 and the distal end of the inner compartment 106*b* to adjust the fluid path and generation of aerosol through the nozzle 142.

The needle 107 may comprise any appropriate material or combination of materials. Exemplary materials useful for the needle 107 include, but are not limited to, metals and metal alloys, for example stainless steel. Fluid that exits the distal end of the inner compartment 106*b* over the surface of the needle 107 is atomized by the flow of gas from the distal end of the outer compartment 106*a*. If the needle 107 is too long (e.g., the needle 107 projecting into the chamber 116), some or all of the fluid may flow down the surface of the needle 107 and come off the distal end of the needle 107 as relatively large droplets. The shape of the aerosol spray that exits the nozzle 142 may also be influenced by the shape of the needle 107 and/or the position of the needle 107 relative to the distal ends of the respective outer compartment 106*a* and inner compartment 106*b*. The shape of the nebulizer 106 and/or nozzle 142 may be configured to provide for a desired spray radius and angle formed by the spray. For example, an angle that is obtuse describes a relatively wider spray radius, while an angle that is acute describes a relatively smaller spray radius. In some examples, the distance between the tip of the needle 107 and the distal end of the inner compartment 106*b* may range from about 5 mm to about 60 mm, such as from about 15 mm to about 25 mm, or from about 15 mm to about 25 mm.

The surface of the needle 107 may be sufficiently smooth such that fluid flows uniformly over the surface to allow for uniform atomization of the fluid. For example, the surface of the needle may be smoothed, e.g., via polishing or similar process. In some examples, the needle 107 may have a surface polished with 800 grit abrasive.

Figure 3A:
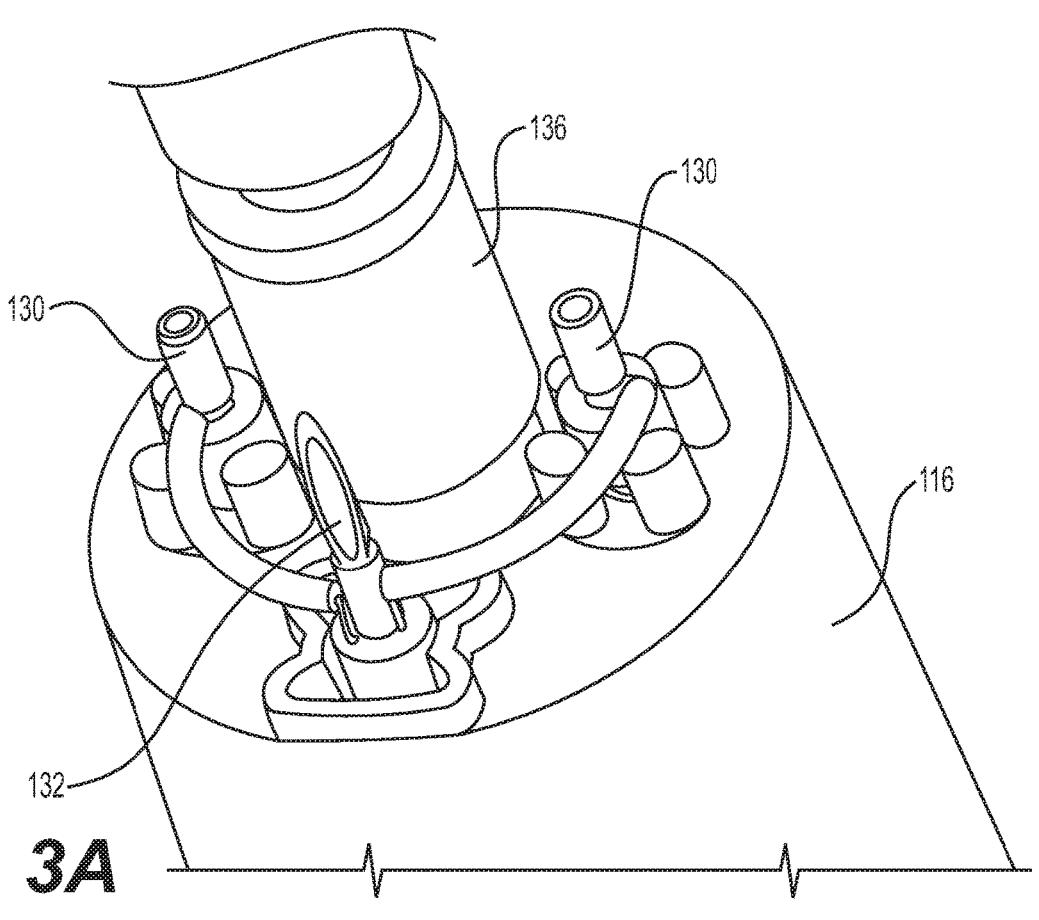
FIGS. 3A and 3B illustrate distal and proximal perspective views, respectively, of a distal end portion of the device of FIG. 1.
Figure 3B:
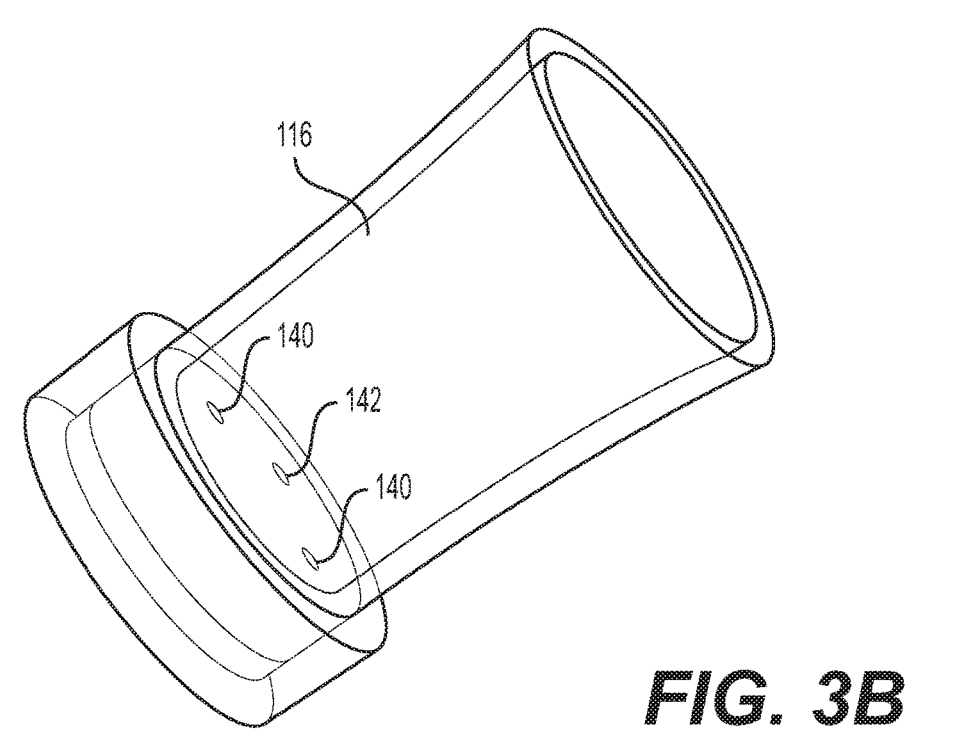

FIGS. 3A and 3B illustrate distal and proximal perspective views, respectively, of the outlet chamber 116. As shown, the proximal side of the outlet chamber 116 may comprise a hypotube 132, at least two electrodes 130, and a housing 136 extending in a proximal direction that encloses the nebulizer 106. The hypotube 132 may be a tubular structure, optionally with a beveled tip, configured to receive the distal tip 182 of the plasma device 180. In some examples, the hypotube 132 is coupled to the chamber 116 by an adhesive, such as a light curing adhesive. The hypotube 132 may comprise any suitable material, such as a metal or metal alloy.

The hypotube 132 may be in communication with the electrodes 130, e.g., via conductive wire. The electrodes 130 may be housed separately, for example, in tubes, wherein the tubes may be connected to the proximal side of the outlet chamber 116 by suitable attachment structures. In some examples, the adapter 120 may comprise only one electrode 130 or more than two electrodes 130. For example, the adapter 120 may include three or more electrodes 130, e.g., arranged in a ring. As mentioned above, the hypotube 132 may be connected to each of the electrodes 130 by a conductive material, for example, copper wire, which may be enclosed by an insulation material such as a polymer coating. The insulated wire may be coupled to the hypotube 132 and secured into place, for example, by an insulation material, such as a silicone tubing sleeve. The silicone tubing sleeve and light curing adhesive may electrically isolate the hypotube 132 and the electrodes 130 in order to minimize electrical energy losses at the junctions of the respective electrodes 130. The electrodes 130 may be housed within a suitable insulating material, for example, plastic or silicone.

In some examples of the present disclosure, the electrodes 130 include pins that may be flush with the wall of the outlet chamber 116, may be recessed, or may protrude into the outlet chamber 116. In at least one example, the pins of the electrodes 130 are recessed or protrude into the chamber 116 by a distance of about 0.1 mm to about 3 mm, such as about 1 mm to about 2.5 mm, or from about 1.5 mm to about 2.0 mm. Without intending to be bound to theory, it is believed that having the pins of the electrodes 130 recessed into the chamber 116 may enhance the intensity of the plasma discharge.

In some examples, the hypotube 132 may have an inner cross sectional area approximately equivalent to the annular outer cross sectional area between the outer surface of the hypotube 132 and the inner surface of the hypotube 132 through the outlet chamber 116. As such, the distance from the hypotube 132 to any point in the gas fluid path, may be relatively small. This may promote uniform exposure of gas to the electrically conductive inner and outer surfaces of the hypotube 132.

The shape, length, and/or diameter of the outlet chamber 116 may be selected in accordance with the desired time for the fluid exiting the nozzle 142 to be exposed to plasma exiting the plasma outlet(s) 140, e.g., to minimize risk of arcing to a surface, e.g., tissue of a subject being treated. As mentioned above, for example, the outlet chamber 116 may have a generally tubular shape as illustrated in FIGS. 1 and 2. The walls of the outlet chamber 116 may flare out to allow for a wider spray of the aerosol and plasma. Without intending to be bound by theory, it is believed that fine atomization of a liquid within a uniform plasma field may promote uniformity of interactions between the plasma and individual molecules of the liquid. The source of gas used to produce the aerosol also may participate in energy transfer from the plasma. In some examples, a high energy arc associated with the plasma may reside substantially or entirely within the inner volume defined by the outlet chamber 116. Thus, there may be insufficient power exiting the outlet chamber 116 for arcing to the tissue of the subject. Approaching or contacting the distal end of the outlet chamber 116 with the tissue surface may block flow of the aerosol and plasma, and serve to quench the arc at the electrode(s) 130. Referring to FIGS. 3A and 3B, the electrodes 130 may open into the outlet chamber 116 through openings 140 in the wall of the chamber 116, which define the plasma outlets 140. As shown in FIG. 3B, the openings 140 may be on either side of nozzle opening 142.

Figure 4:
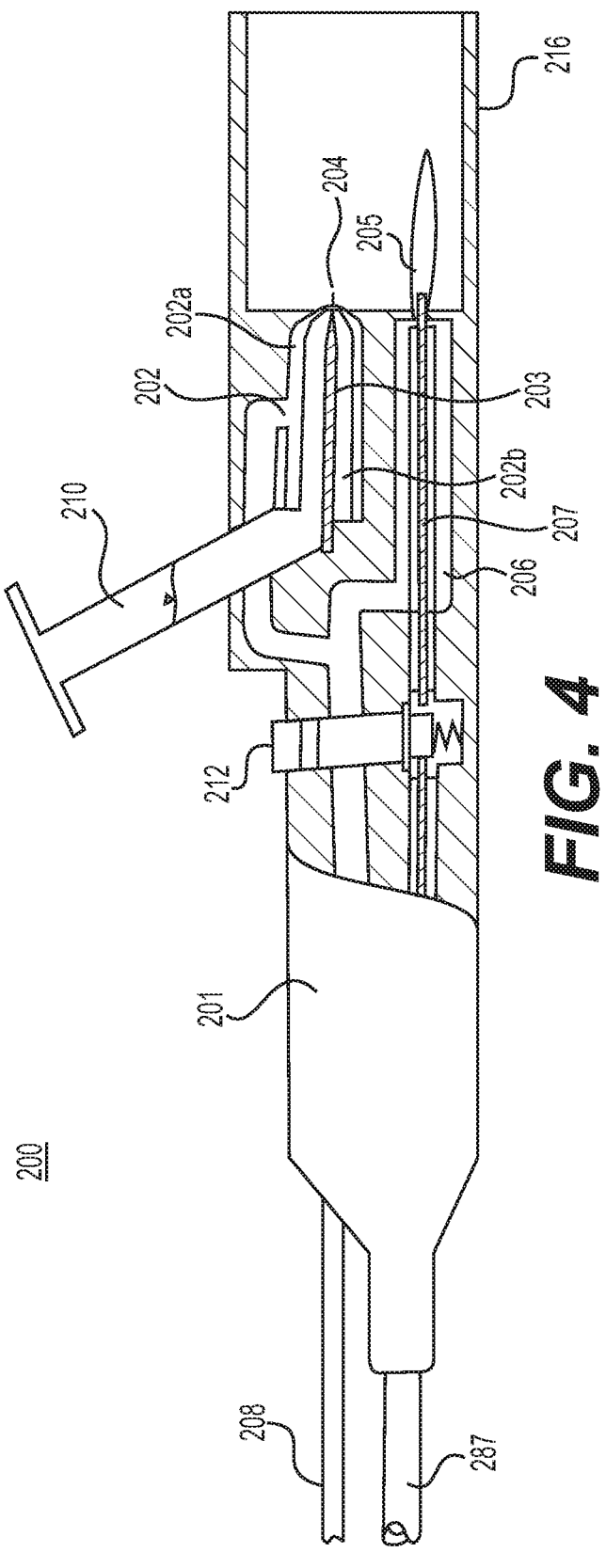
FIG. 4 illustrates another exemplary device, in accordance with some aspects of the present disclosure.

The features of the adapter 120 optionally may be integrated into a plasma device. FIG. 4 illustrates an exemplary device 200 according to the present disclosure, comprising a body 201, gas tube 208, fluid reservoir 210, actuator 212, outlet chamber 216, and cable generator 287. The gas tube 208 may supply gas to the device 200 for generating aerosol and plasma. The cable generator 287 may provide a source of electricity to generate plasma. While FIG. 4 shows the gas tube 208 separate from the cable generator 287, in some examples, the cable generator 287 may also provide a source of gas.

The device 200 may include any of the features of the adapter 120 and/or plasma device 180 above. For example, similar to the nebulizer 106 described above in connection to the adapter 120, the nebulizer 202 of the device 200 as illustrated comprises an outer compartment 202a, an inner compartment 202b, a needle 203, and a nozzle 204. The outer compartment 202a may receive gas from the gas tube 208, and the inner compartment 202b may receive fluid from the fluid reservoir 210. The fluid thus exits the inner compartment 202b over the distal end of the needle 203 to combine with gas exiting the outer compartment 202a, such that the fluid becomes atomized and exits through the nozzle 204 as aerosol into the outlet chamber 216.

The fluid reservoir 210 shown in FIG. 4 is integrated into the device 200, such that the fluid reservoir 210 is not removable. In such cases, the fluid reservoir 210 may optionally be configured to allow for refilling of fluid. In other examples, the fluid reservoir 210 may be coupled to the device 200 via complementary mating elements, such that the fluid reservoir 210 may be refilled or replaced as needed by removing the fluid reservoir 210 from the device 200.

Once the device 200 is turned on via actuator 212, gas and electric current may be concurrently delivered to the device 200. The gas may produce a pressure difference that draws fluid from the fluid reservoir 210 into the nebulizer 201, atomize the fluid so that it flows out of the nozzle 204 and into the outlet chamber 216. The gas also may enter a compartment 206 housing the electrode in order to generate a plasma in the outlet chamber 216. Thus, for example, electric current may be supplied to the electrode 207 to produce a plasma in the gas that enters the outlet chamber 216 via plasma outlet 205. An exemplary image of a plasma plume is illustrated in FIG. 4.

FIGS. 5A-5E illustrate examples of fluid reservoirs that may be used with the adapter 120, the device 200, and any other devices disclosed herein. In some examples, the fluid reservoir may be integrated into the device, similar to fluid reservoir 210 illustrated in FIG. 4.

Figure 5B:
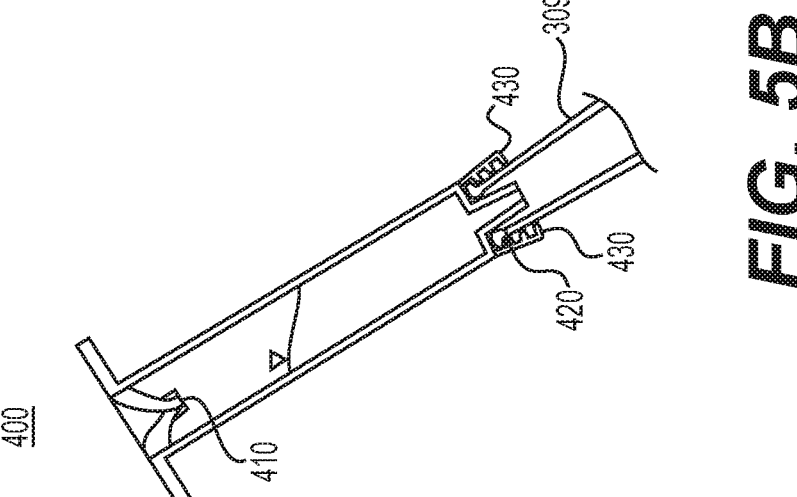
FIGS. 5A-5E illustrate exemplary fluid reservoirs, in accordance with some aspects of the present disclosure.
Figure 5A:
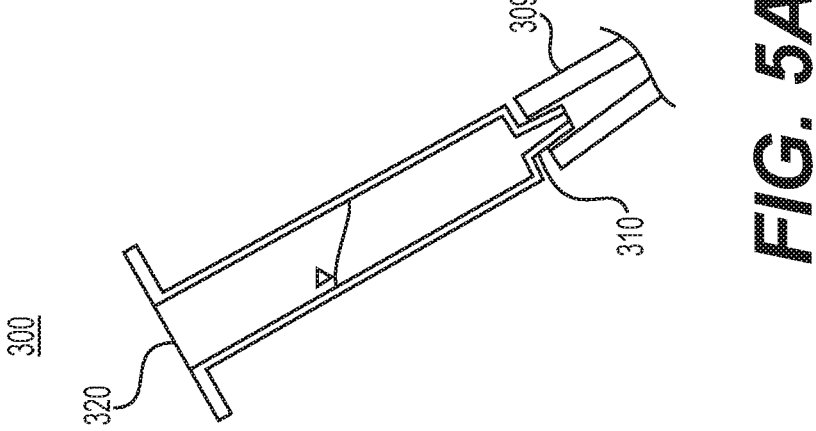

The fluid reservoirs shown in FIGS. 5A and 5B may be in the form of syringes configured to be coupled to a fluid inlet of a device. FIG. 5A illustrates a fluid reservoir 300 with a tapered adapter 310, configured to be received by the fluid inlet 309 of the device. The top 320 of the fluid reservoir may be open or closed. For example, the fluid reservoir may be single use or may include an open top or an inlet suitable for introducing additional fluid. For example, FIG. 5B illustrates a fluid reservoir 400 wherein the top of the reservoir 400 includes a one-way valve 410. Thus, for example, the fluid reservoir 400 may be filled or refilled with a fluid, e.g., while avoiding loss of fluid. As illustrated in FIG. 5B, the fluid inlet 309 of the device may include mating elements 430 complementary to mating elements 420 of the reservoir 400. For example, the complementary mating elements may include threads, a luer-lock connection, clips, etc.

Figure 5D:
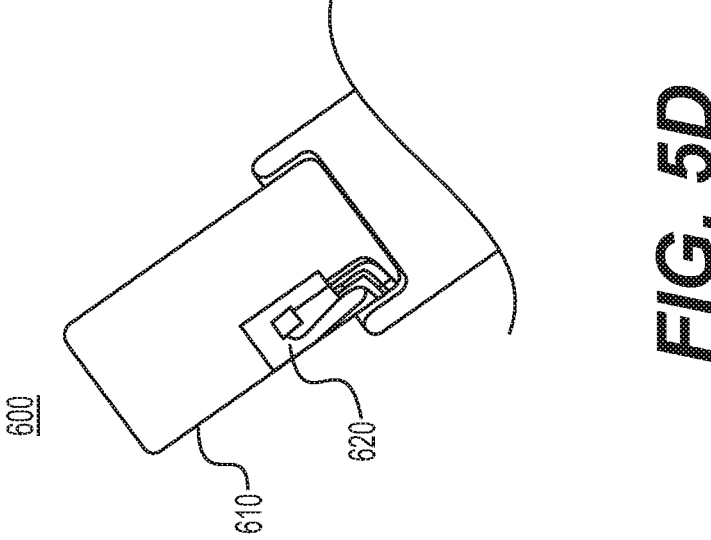
Figure 5C:
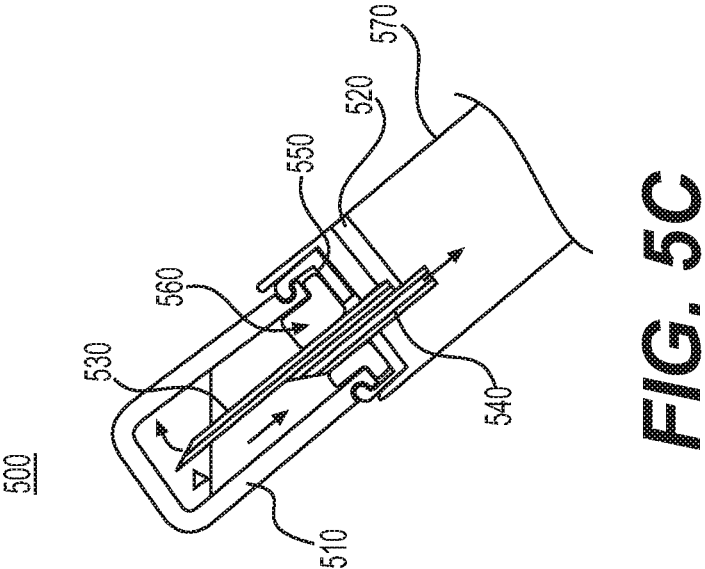
Figure 5E:
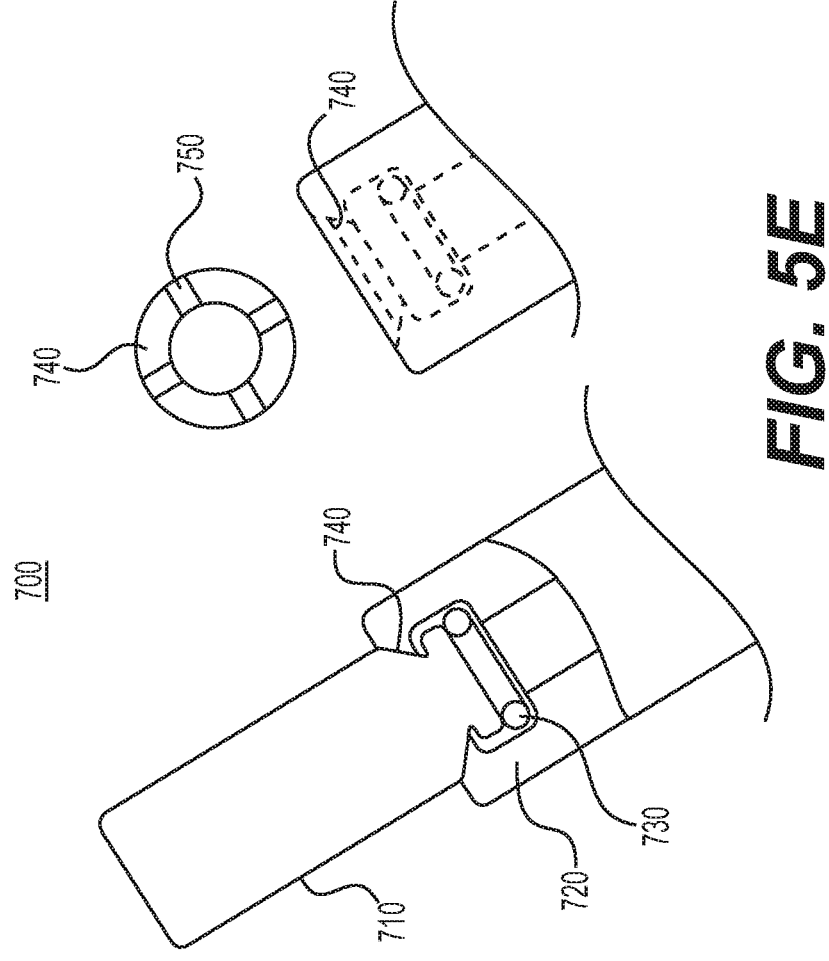

Referring to FIGS. 5C, 5D, and 5E, the fluid reservoirs suitable for the devices herein may have various shapes other than syringes, for example, a vial, bottle, or tube. The fluid reservoir 500 of FIG. 5C is shown in the form of a vial 510 comprising two needles 530, 540 (e.g., dual hypodermic needles) configured to allow for venting of the vial 510 and feeding the fluid into the device, e.g., via a fluid inlet 570 of the device in communication with a nebulizer. When dual needles 530, 540 are used, air or other gas at atmospheric pressure may flow through a fluid channel 520 into a first needle 530, and fluid in the vial 510 may exit the reservoir 500 through a second needle 540. The vial 510 may also include a vial cap 550 and stopper 560, e.g., to prevent liquid from spilling out. The vial cap 550 and stopper 560, may comprise any appropriate material, for example, rubber or silicone.

According to some aspects of the present disclosure, the fluid reservoir may be configured to receive and/or transmit data regarding the fluid reservoir. For example, FIG. 5D illustrates an exemplary fluid reservoir 600 that includes a vial 610 (which may be similar to vial 510 of FIG. 5C) or other suitable container, such as a syringe, comprising an electronic chip 620. The electronic chip may include one or more sensors configured to collect data and measurements and/or processors to perform various algorithms. The electronic chip 620 may be disposed on an exterior portion of the fluid reservoir, e.g., vial 610, as illustrated in FIG. 5D, may be coupled to an interior portion or surface of the fluid reservoir (and may be electrically isolated from fluid contained in the fluid reservoir), or may be integrated into a wall of the fluid reservoir. The electronic chip 620 may be preprogrammed to recognize or measure one or more parameters and/or characteristics of the devices or components thereof disclosed herein. Exemplary parameters may include dosing information (e.g., the number of possible doses to be administered per vial), the type of fluid in the vial, characteristics of the fluid in the vial such as, e.g., viscosity, temperature, volume, pH. The fluid reservoir 600 may be electronically coupled to the device and/or a generator/power source used with the device to allow for transmission of data and/or powering electronic components. In some examples, the electronic chip 620 may be configured to receive and/or transmit data.

The fluid reservoir 700 as illustrated in FIG. 5E includes a vial 710 (or other suitable type of container) with mating elements complementary to mating elements of a fluid inlet 720 of the device. Thus, the fluid reservoir 700 may be selectively coupled to, and removed from, the device. The fluid inlet 720 of the device may include a fastener defining a surface 740, which may be tapered, for receiving the fluid reservoir 700. The surface 740 defines at least one slot 750 or a plurality of slots 750 that allow(s) the surface 740 to flex to grip onto the opening of the vial 710.

FIG. 5E shows three images: the vial 710 coupled to the fluid inlet 720 of a device, a side view of the fluid inlet 720 with features of the fastener including surface 740 and a central fluid channel shown in dotted lines, and a top-down view of just the surface 740 including four slots 750. In some examples, the surface 740 may include only one slot 750, or may include two slots 750, three slots 750, or five or more slots 750, which may be regularly spaced along the surface 740. The fastener may comprise a flexible or malleable material, such as silicone, rubber, or other flexible polymer, or may comprise a more rigid or semi-rigid material, e.g., plastic, wherein the slots 750 provide sufficient clearance or flexibility to allow the tapered surface 740 to accommodate and grip the vial 710 to avoid relative movement between the fluid inlet 720 and the vial 710. In some examples, the vial 710 may include features to facilitate a tight grip. For example, the vial 710 may comprise a seal 730 to secure the vial 710 in the fluid inlet 720 of the device. The vial 710 may be a single-use vial or may be configured to be refilled and re-used.

Figures 6A, 6B, 6C:
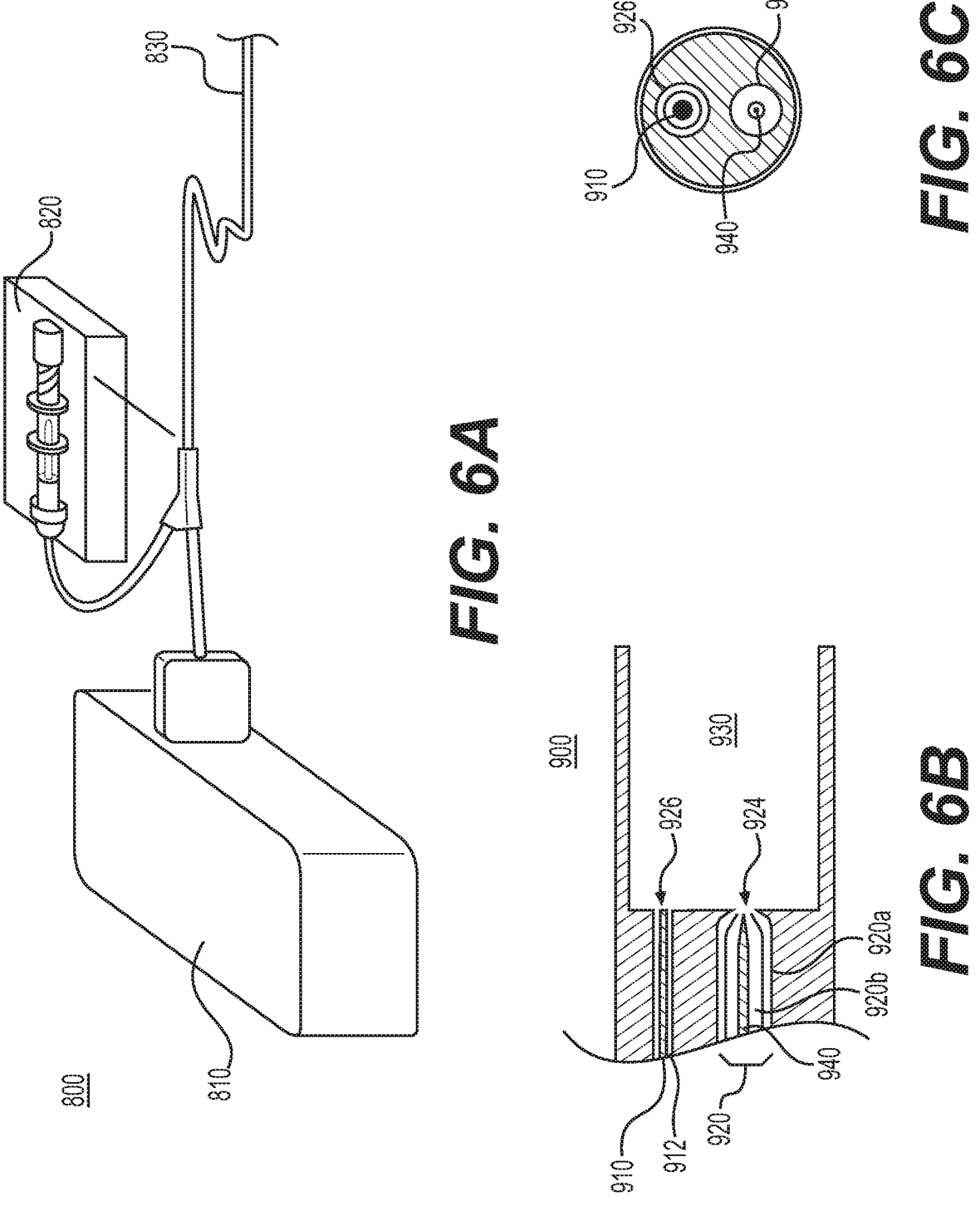
FIG. 6A illustrates an exemplary catheter system, in accordance with some aspects of the present disclosure.
FIGS. 6B and 6C show an exemplary distal end of the catheter of the system.

The devices herein may be configured for treatment of external and/or internal tissue. FIG. 6A illustrates an exemplary catheter system 800 for treating internal tissue of a subject. For example, the system 800 may be used in endoscopic, cystoscopic, and/or laparoscopic procedures. The system 800 as shown includes a plasma generator 810, a syringe pump 820, and a catheter 830. The plasma generator 810 may be used to provide gas and/or electricity to the catheter. In some examples, gas may be provided to the catheter 830 via a separate gas source, independently of the plasma generator 810. The syringe pump 820 may be any suitable syringe system for providing fluid to the catheter 830. For example, the syringe pump 820 may be operated manually or automatically, e.g., via a user interface that conveys instructions to electronic components of the syringe pump 820.

FIG. 6B illustrates an exemplary distal end 900 of the catheter 830, and FIG. 6C shows an end view of FIG. 6B. As shown in FIG. 6B, the catheter 820 may house an electrode 910, a nebulizer 920, and define an outlet chamber 930 at the distal end 900. The nebulizer 920 may comprise an outer compartment 920a, an inner compartment 920b, and a needle 940, which may be similar to components of nebulizers 106 and 202 described above in connection to adapter 120 and device 200. The electrode 910 may be housed in an electrode compartment 912 of the catheter 830. Once the syringe pump 820 is activated to allow fluid to flow to the inner compartment 920b of the catheter 830, and the plasma generator 810 is turned on to allow gas to flow to the outer compartment 920a and the electrode compartment 912, and to supply electricity to the electrode compartment 912, the electric current generates a plasma and an aerosol that enter the outlet chamber 930. The aerosol exits nebulizer 920 via a nozzle 924, and the plasma exits the electrode compartment 912 via plasma outlet 926.

Figure 7B:
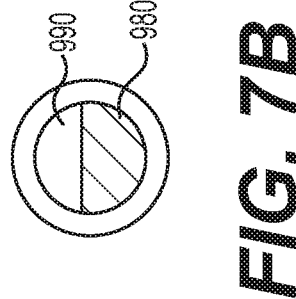
FIGS. 7A and 7B illustrate another exemplary distal end of the catheter system of FIG. 6A, in accordance with some aspects of the present disclosure.
Figure 7A:
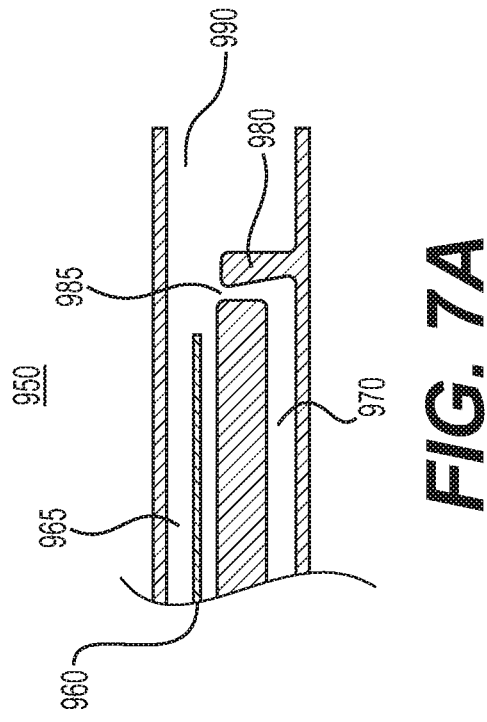

Another example of a distal end 950 of the catheter 830 of catheter system 800 is illustrated in FIGS. 7A and 7B. The catheter 830 may include a fluid compartment 970, an electrode 960 housed in electrode compartment 965, and an outlet chamber 990. Gas and electricity supplied to the electrode compartment 965 and the electrode 960, respectively, may generate a plasma as described above. The plume of the plasma may extend at least partially into the outlet chamber 990. The distal end of the fluid compartment 970 is closed by a wall 980 that causes fluid to change direction and pass through a narrowed aperture of a nozzle 985, generating an aerosol. The aerosol thus comes into contact with the plasma and mixes with energized species of the plasma within the outlet chamber 990. FIG. 7B shows an end view of the distal end 950 of the catheter 830, including the outlet chamber 990 and the wall 980.

The types of catheter systems 800 illustrated in FIGS. 6A-6C and 7A-7B may be used in a variety of medical procedures to treat internal tissue, including, e.g., endoscopic, cystoscopic, and/or laparoscopic procedures as mentioned above. In at least one example, the catheter system may be used in a tissue removal and/or tissue ablation process. For example, a therapeutic agent such as collagen (or any of the other exemplary therapeutic agents described herein) may be deposited on an internal tissue surface after tissue removal or ablation using a catheter system as disclosed herein. In at least one example, cancerous or pre-cancerous tissue (e.g., cancerous or pre-cancerous tissue of the gastrointestinal tract, such as esophagus, stomach, intestine, etc.) may be treated with the catheter systems disclosed herein.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents that all fall in the scope of the aspects described herein. Accordingly, the present disclosure is not to be considered as limited by the foregoing description.

What is claimed is:

1. A medical device comprising:
a housing that includes a nebulizer, the nebulizer comprising:
 an outer compartment in communication with a gas inlet,
 an inner compartment in communication with a fluid channel and a fluid inlet, and
 a needle;
 wherein the needle is radially inward of the inner compartment, the inner compartment is radially inward of the outer compartment, and a distal end of the outer compartment is in communication with a distal end of the inner compartment;
at least one electrode; and
a chamber defined by a distal end portion of the housing;
wherein a distal-facing surface of the chamber defines at least one plasma outlet and a nozzle in communication with the nebulizer; and
wherein an end of the at least one electrode is proximate the plasma outlet, and wherein a proximal portion of the chamber is configured to receive an electrode tip of a plasma device and to electrically connect the electrode tip of the plasma device to the at least one electrode.

2. The medical device of claim 1, wherein a longitudinal position of the needle of the nebulizer is adjustable.

3. The medical device of claim 1, wherein a distal portion of the housing includes an actuator configured to control the flow of a gas to the gas inlet.

4. The medical device of claim 3, further comprising the plasma device, wherein the actuator of the housing is arranged relative to an actuator of the plasma device so as to allow a user to control the flow of gas and to power the plasma device simultaneously.

5. The medical device of claim 1, further comprising a fluid reservoir coupled to the fluid inlet.

6. The medical device of claim 5, wherein the fluid reservoir includes mating elements complementary to mating elements of the fluid inlet, such that the fluid reservoir is selectively detachable from the fluid inlet.

7. The medical device of claim 5, wherein the fluid reservoir contains a liquid that comprises at least one therapeutic agent.

8. The medical device of claim 7, wherein the at least one therapeutic agent comprises a biomolecule, a pharmaceutical agent, or a combination thereof.

9. The medical device of claim 7, wherein the at least one therapeutic agent is dissolved in a solvent.

10. The medical device of claim 1, wherein the housing defines a first channel in communication with the outer compartment of the nebulizer and a second channel that contains the at least one electrode, a distal end of the second channel defining the plasma outlet.

11. The medical device of claim 1, wherein the at least one electrode extends through a wall of the chamber.

12. A medical device comprising:

a housing that includes a nebulizer, the nebulizer comprising:

an outer compartment, an inner compartment, and a needle;

wherein the needle is radially inward of the inner compartment, the inner compartment is radially inward of the outer compartment, and a distal end of the outer compartment is in communication with a distal end of the inner compartment;

a fluid reservoir coupled to a fluid inlet, the fluid reservoir containing a liquid that comprises at least one therapeutic agent;

at least one electrode; and a chamber defined by a distal end portion of the housing;

wherein a distal-facing surface of the chamber defines at least one plasma outlet and a nozzle in communication with the nebulizer; and wherein an end of the at least one electrode is proximate the plasma outlet; and wherein a proximal portion of the chamber is configured to receive an electrode tip of a plasma device and to electrically connect the electrode tip of the plasma device to the at least one electrode.

13. The medical device of claim 12, wherein the fluid reservoir includes mating elements complementary to mating elements of the fluid inlet, such that the fluid reservoir is selectively detachable from the fluid inlet.

14. The medical device of claim 12, wherein the fluid reservoir is permanently attached to the fluid inlet.

15. The medical device of claim 12, wherein the outer compartment of the nebulizer is in communication with a gas inlet, and the inner compartment of the nebulizer is in communication with the fluid inlet.

16. The medical device of claim 12, wherein the end of the at least one electrode is recessed from the distal-facing surface of the chamber.

17. The medical device of claim 12, wherein the housing defines a first channel in communication with the outer compartment of the nebulizer and a second channel that contains the at least one electrode, a distal end of the second channel defining the plasma outlet.

18. The medical device of claim 12, wherein the at least one therapeutic agent comprises a biomolecule, a pharmaceutical agent, or a combination thereof.

19. A medical device comprising:

a housing that includes a nebulizer, the nebulizer comprising:

an outer compartment in communication with a gas inlet, an inner compartment in communication with a fluid inlet, and a needle;

wherein the needle is radially inward of each of the inner compartment and the outer compartment, and a distal end of the outer compartment is in communication with a distal end of the inner compartment;

at least one electrode;

a fluid reservoir coupled to the fluid inlet; and a chamber defined by a distal end portion of the housing;

wherein a distal-facing surface of the chamber defines at least one plasma outlet and a nozzle in communication with the nebulizer; and wherein an end of the at least one electrode is proximate the plasma outlet; and wherein a proximal portion of the chamber is configured to receive an electrode tip of a plasma device and to electrically connect the electrode tip of the plasma device to the at least one electrode.

20. A method of treating tissue of a subject, the method comprising exposing the tissue to plasma and an aerosol comprising at least one therapeutic agent using a medical device, the medical device comprising:

a housing that includes a nebulizer, the nebulizer comprising:

an outer compartment in communication with a gas inlet, an inner compartment in communication with a fluid channel and a fluid inlet, wherein the fluid channel receives a fluid that comprises the at least one therapeutic agent, and a needle;

wherein the needle is radially inward of the inner compartment, the inner compartment is radially inward of the outer compartment, and a distal end of the outer compartment is in communication with a distal end of the inner compartment;

at least one electrode; and a chamber defined by a distal end portion of the housing;

wherein a distal-facing surface of the chamber defines at least one plasma outlet and a nozzle in communication with the nebulizer;

wherein an end of the at least one electrode is proximate the plasma outlet;

wherein a proximal portion of the chamber receives an electrode tip of a plasma device and electrically connects the electrode tip of the plasma device to the at least one electrode; and wherein the plasma device generates the plasma and the nebulizer generates the aerosol exposed to the tissue.

21. The method of claim 20, wherein the tissue is internal tissue or external tissue.

22. The method of claim 20, wherein the tissue is part of a wound, burn, cut, ulcer, abrasion, or tumor.

23. The method of claim 20, wherein the subject is a human subject.

24. The method of claim 20, wherein the method comprises generating plasma at a frequency ranging from about 150 kHz to about 500 kHz.

25. The method of claim 20, wherein the at least one therapeutic agent comprises a biomolecule, a pharmaceutical agent, or a combination thereof.

26. The method of claim 20, wherein the at least one therapeutic agent comprises collagen.

27. The method of claim 20, wherein the method includes supplying the fluid to the nebulizer from a fluid reservoir and supplying power to the at least one electrode simultaneously, such that the aerosol exits the nozzle at the same time the plasma exits the plasma outlet.

28. The method of claim 27, wherein supplying the fluid and supplying the power includes pressing a single actuator of the medical device.

29. The method of claim 28, wherein pressing the single actuator engages a power button of the medical device aligned with the single actuator.

\* \* \* \* \*